United States Patent [19]

Beretsky et al.

[11] 4,063,549
[45] Dec. 20, 1977

[54] ULTRASONIC METHOD AND APPARATUS FOR IMAGING AND CHARACTERIZATION OF BODIES

[75] Inventors: Irwin Beretsky, New City; Bernard Lichtenstein, Yorktown Heights, both of N.Y.

[73] Assignee: Technicon Instruments Corporation, Tarrytown, N.Y.

[21] Appl. No.: 643,732

[22] Filed: Dec. 22, 1975

[51] Int. Cl.² .............................................. A61B 10/00
[52] U.S. Cl. ....................................... 128/2 V; 73/574; 73/610; 128/2.05 Z
[58] Field of Search .................. 128/2 V, 2 R, 2.05 Z, 128/2.1 Z; 73/67.1, 67.9

[56] References Cited
U.S. PATENT DOCUMENTS

| | | | |
|---|---|---|---|
| 3,830,223 | 8/1974 | Beretsky et al. | 128/2 V |
| 3,856,985 | 12/1974 | Yokoi et al. | 128/2 V X |
| 3,934,458 | 1/1976 | Beretsky et al. | 73/67.9 |

*Primary Examiner*—Kyle L. Howell

*Attorney, Agent, or Firm*—S. P. Tedesco; James J. Romano, Jr.

[57] ABSTRACT

Method and apparatus are provided for the determination of the Raylographic information of a body part which is ensonified by acoustical energy pulses by a particularly precisely focused acoustical focusing system to produce acoustical energy echo pulses which are detected in coherent manner. Fourier transformation of the pulses from the time to the frequency domain enables frequency domain deconvolution to provide the impulse response with minimization of mathematical instabilities and distortion of the frequency domain impulse response. Noise extraction and spatial deconvolution filtering are included to respectively maximize signal to noise ratio and minimize distortive effects of body part surface non-orthogonality and combine with the above to provide for particular stability in the overall results and attendant increase in the axial resolution of Raylographic display and in the overall resolution of body part image displays.

35 Claims, 16 Drawing Figures

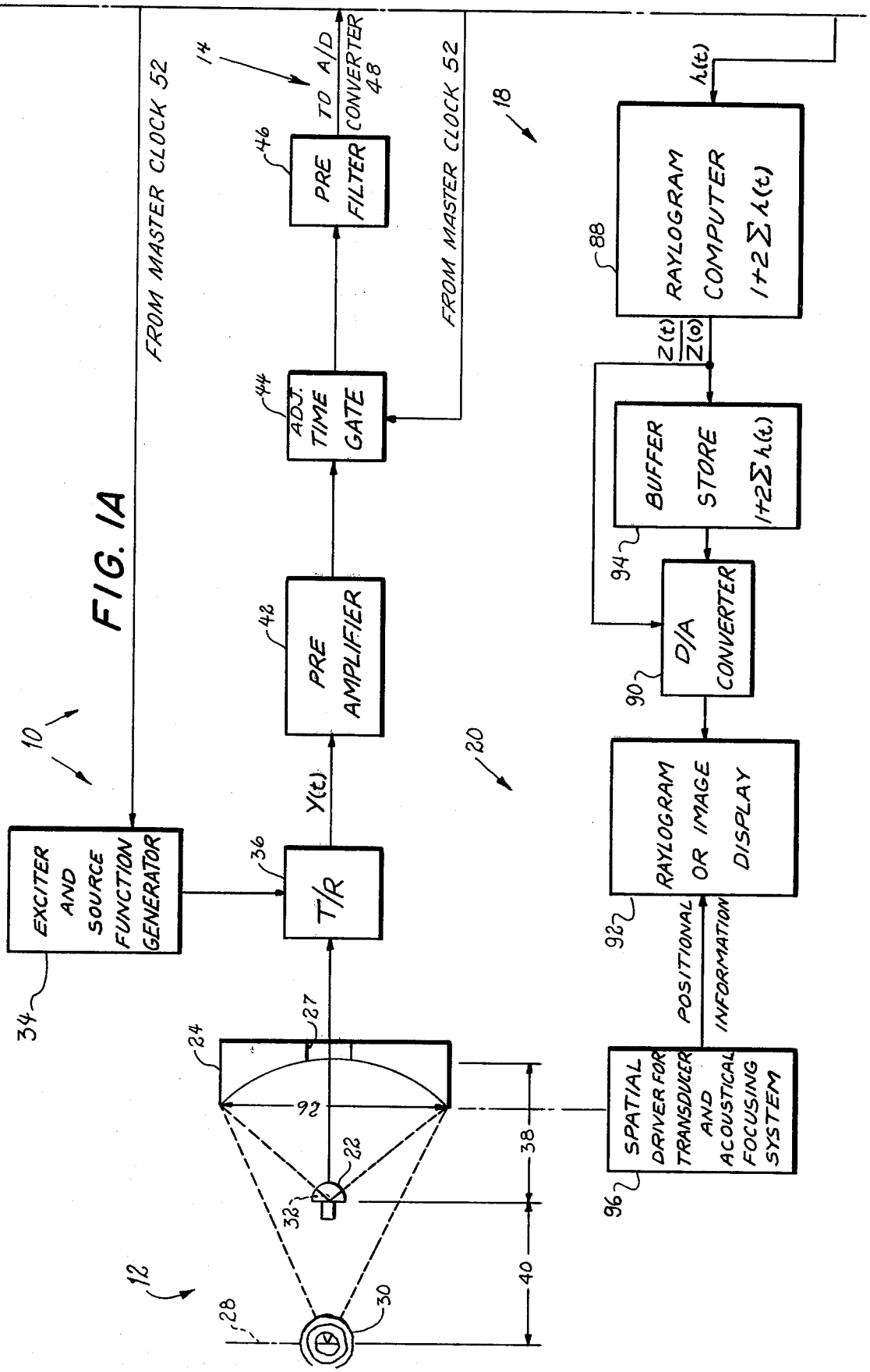

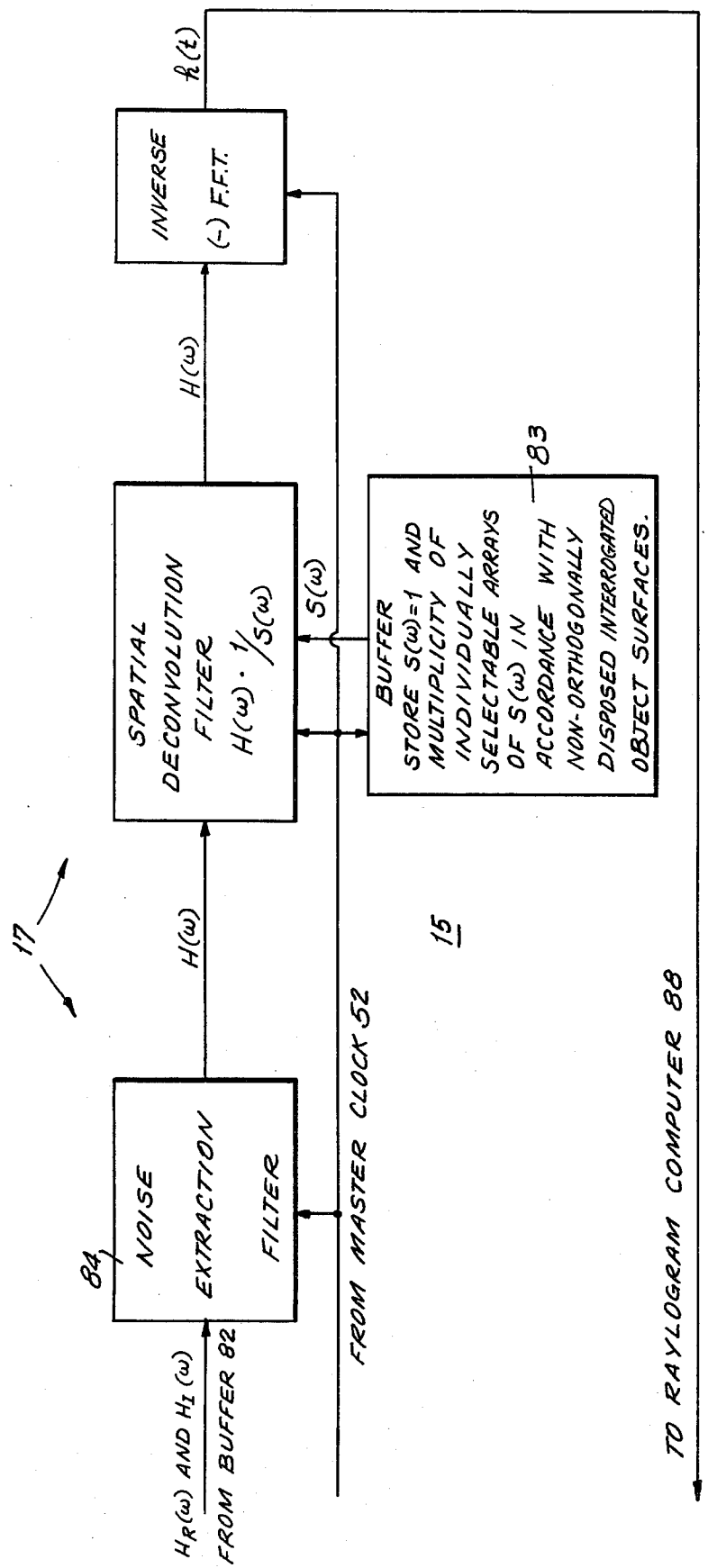

RAYLOGRAM

ULTRASONIC METHOD AND APPARATUS FOR IMAGING AND CHARACTERIZATION OF BODIES

BACKGROUND OF THE INVENTION

1. Field of the Invention

This invention relates to new and improved ultrasonic method and apparatus for non-invasive biophysical diagnosis.

2. Description of the Prior Art.

Although prior art acoustical interrogation methods and apparatus in the nature of those disclosed, for example, in our U.S. Pat. No. 3,830,223 of Aug. 20, 1974 entitled "Methodology And Apparatus For Non-Invasive Biophysical Diagnosis," are known which effect coherent detection, i.e. detection of both amplitude and phase in the reflected acoustical energy pulses, and which operate through deconvolution of the echo signal train to provide a particularly precise impedance profile of the acoustically interrogated material, it may be understood that such prior art methods and apparatus operate to mathematically deconvolve the echo signal train in the time domain. This time domain deconvolution can, under conditions of certain echo signal train characteristics, result in mathematical instabilities in the deconvolution equation which are difficult to discover and overcome, and which can in turn result in loss of some of the information bearing attributes of the echo signal train with attendant degradation of the provided impedance profile resolution. In addition, essential echo signal processing techniques such as amplification and filtering are, under certain conditions, rendered difficult by time domain deconvolution. Too, it may be understood that the essential source function characteristics in the nature of bandwidth, and the overall characteristics of the acoustical focusing apparatus and methods of the prior art are, in many instances, not determined and/or operable with sufficient preciseness to afford high degrees of resolution and are not, in any event, suitably interrelated with the echo signal train deconvolution equation to maximize the mathematical stability of the latter.

OBJECTS OF THE INVENTION

It is, accordingly, an object of this invention to provide new and improved ultrasonic method and apparatus which are operable to maximize the number of the information bearing attributes of the echo signal train which are obtained to thus maximize the accuracy and clarity of the provided results.

Another object of the invention is the provision of method and apparatus as above wherein echo signal train deconvolution is effected in the frequency domain to minimize and render more readily remediable mathematical instabilities in the deconvolution equation, to simplify essential pre and post deconvolution echo signal train processing techniques, and to render more stable the provided results.

Another object of the invention is the provision of method and apparatus as above wherein the essential characteristics of the source function and acoustical focusing system are precisely and specifically determined to minimize instabilities in the echo signal train deconvolution procedure.

A further object of the invention is the provision of method and apparatus as above which are effective to significantly improve acoustical axial resolution and, when coupled with acoustical B scan tomography, to significantly improve the overall image resolution.

SUMMARY OF THE DISCLOSURE

As disclosed herein, the new and improved method and apparatus of the invention comprise the ensonification of at least a portion of a body part with acoustical energy pulses, the coherent detection of the resultant echo pulses, and the processing of the latter to provide indicia of the relative acoustic impedance of the ensonified body part. This is accomplished by the Fourier transformation of the ensonifying energy and echo pulses from the time to the frequency domain and the deconvolution thereof by deconvolution filter means to provide the impulse response in the frequency domain of the ensonified body part throughout a predetermined frequency range. The mathematical stability of the deconvolution process is insured by the replacement of zero values in the deconvolution equation denominator by non-zero values which are precisely calculated to have minimal distortive effect on the provided frequency domain impulse response; and noise extraction filtering is effected to provide for maximization of the signal to noise ratio of the latter. Thereafter, the impulse responses are Fourier transformed from the frequency to the time domain to provide the impulse response to the ensonified body part, and the Raylographic information of interest calculated therefrom. A particularly precisely focused acoustical focusing system is utilized for body part ensonification and coherent echo pulse detection to, in combination with the particularly stable Raylographic information provided as described above, make possible the particularly high resolution imaging or characterization of the ensonified body part through use of appropriate scanning and display device display mode techniques. Spatial deconvolution filter means are included to minimize the distortive effect of non-orthogonally disposed body part surfaces to further enhance resolution. In addition, piezoelectric echo pulse detection means are disclosed which may be incorporated into the acoustical focusing system to provide for dynamic system focusing in the absence of system movement.

DESCRIPTION OF THE DRAWINGS

The above and other objects and significant advantages of our invention are believed made clear by the following detailed description thereof taken in conjunction with the accompanying drawing wherein:

FIGS. 1A, 1B and 1C are a connected schematic and/or block diagram illustrating the configuration of apparatus in accordance with the teachings of this invention;

DETAILED DESCRIPTION OF THE INVENTION

Figure 1B:
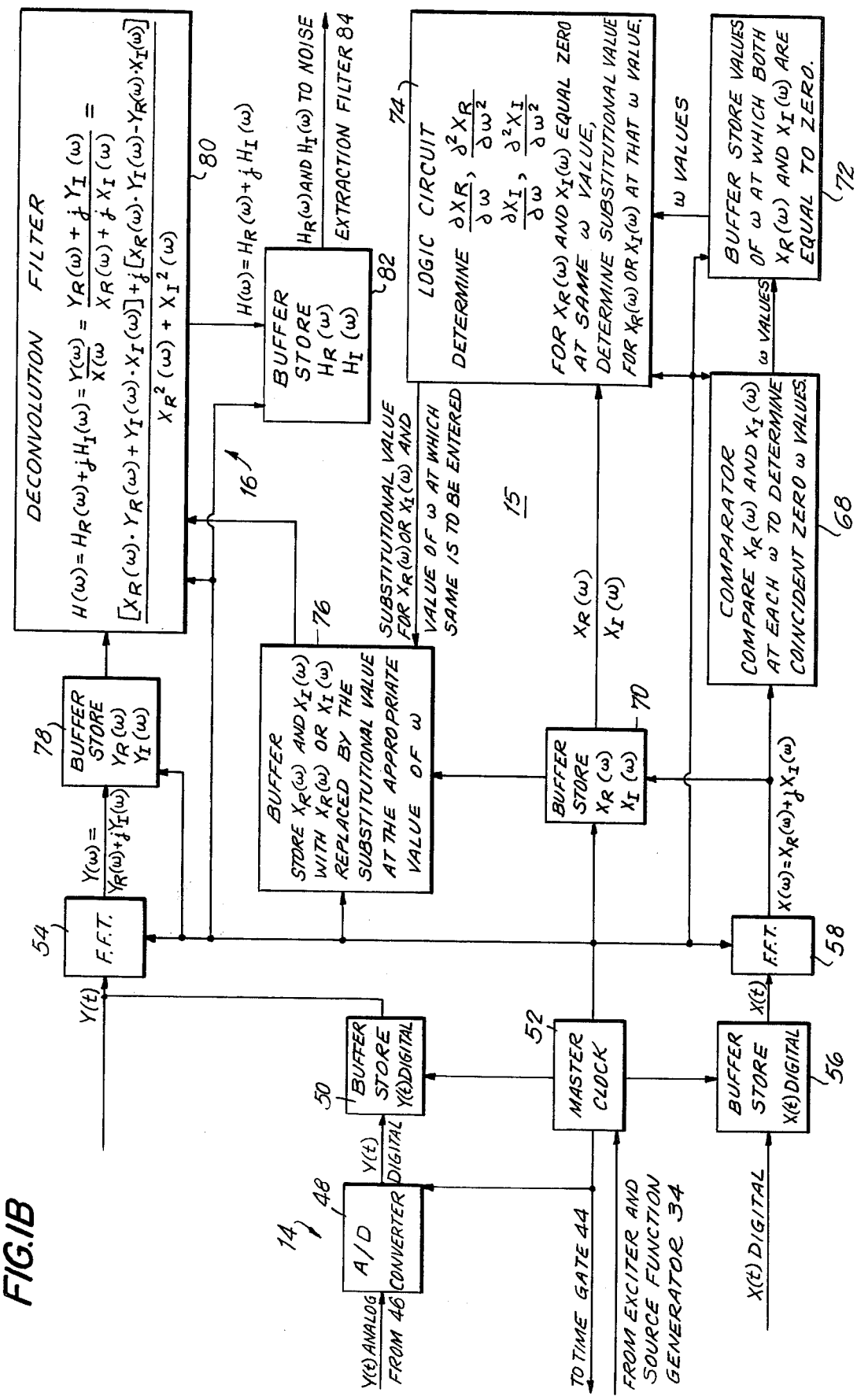

Referring now to FIG. 1, ultrasonic apparatus constructed and operative in accordance with the teachings of our invention is indicated generally at 10 and comprise a transducer control and acoustical focusing system as indicated generally at 12, analog signal processing and analog/digital conversion means as indicated generally at 14, an impulse response computer indicated generally at 15 which includes a deconvolution filter network as indicated generally at 16 and noise extraction and spatial deconvolution filter means as indicated generally at 17, a Raylogram or impedance profile computer as indicated generally at 18, and Raylogram storage and Raylogram and/or image display means as indicated generally at 20.

The focusing 12 comprises a highly damped convex receiver/projector transducer 22, and an elliptical acoustical reflector 24 forming a large acoustical aperture 26 and having a central relief hole 27. The system 12 is arranged to have two acoustical focci, one at the system focal plane 28 which intersects the layered object 30 to be acoustically interrogated, and the other at the transducer 22 as indicated at 32; it being understood by those skilled in this art that the phrase "acoustical focusing" as used regarding the system 12 means that all of the frequency components of the transmitted and reflected acoustical energy at the wavelengths under consideration will, within the limits of diffraction, arrive at the same point in space at the same time. The two such points of primary interest in system 12 are the system focus at focal plane 28 and the focus 32 at transducer 22. The surface of the transducer 22 is spherical with the radius of curvature thereof having its center at focal point 32.

The design of reflector 24 is derived from geometrical calculations and the focal points can be considered, in each instance, as the centroid of a finite reflector focal volume when the wavelengths which are transmitted are not infinitesimal. In the axial symmetric case this finite focus volume may be envisioned as the volume defined by a cylindrical surface, with the end face of the cylinder perpendicular to and colinear with the major axis of the relevant ellipsoid. The focal point, geometrically defined, is located within this cylindrical surface, along the major axis, and midway between the two end surfaces of the cylinder. The diameter of the end surfaces, and thus of the focal volume, is related to the wavelengths of the transmitted component frequencies of the acoustical signal; and it may be understood that the lowest frequency signal component capable of being focused exhibits maximum energy on the axis of this focal volume.

An exciter and source function generator is indicated at 34 and an electronic transmit and receive switch at 36, and the same are operatively connected as shown to transducer 22 for obvious purpose.

Acoustical interrogation of a layered material 30 by acoustical focusing system 12 to determine the relative specific acoustical impedance of the respective material layers will result in acoustical echo pulses which will be received and transduced by transducer 22 and applied in an appropriately timed manner as electrical echo signals from electronic transmit and receive switch 36 to broad band, low noise preamplifier 42 of appropriate frequency response. A representative form of one such electrical echo signal or echo train is indicated by the waveform Y(t) in FIG. 2A which is a plot of signal amplitude as a function of time, and it is of interest to note that both amplitude and phase information are preserved in this signal in the manner characteristic of coherent echo signal train detection.

The particularly significant advantages of coherent detection as compared, for example, to energy detection may be readily understood to include retention of acoustical impedance polarity, prevention of loss of fine boundary detail as a function of the integration time constant which must be utilized in energy detection but which is not utilized in coherent detection, and the maintenance of a fixed reference impedance, all of which combine to enable a more complete characterization of, for example, the property of the body tissue under interrogation and thus provide a higher probability of detection of the presence of a pathologic condition. Coherent detection, and the ability thereof to detect and thus enable the display of fine boundary detail, is equivalent to being able to determine the epoch times of each acoustical echo from the interrogated material boundaries with greater precision, thereby generating information which can be used to produce images of the body with significantly higher resolution than can be obtained by the use of energy detection techniques. Coherent detection, as based upon a "comparison" to a known transmitted acoustical signal source, can produce image resolution which would only be obtainable by energy detection techniques through use of higher frequency source functions which are of course subject to the obvious limitations regarding depth penetration and irreverible absorption of the higher frequency source function components by body tissue structure. A number of these advantages are disclosed in greater detail in our U.S. Pat. No. 3,830,223, the disclosure of which is hereby incorporated by reference herein.

Figure 2A:
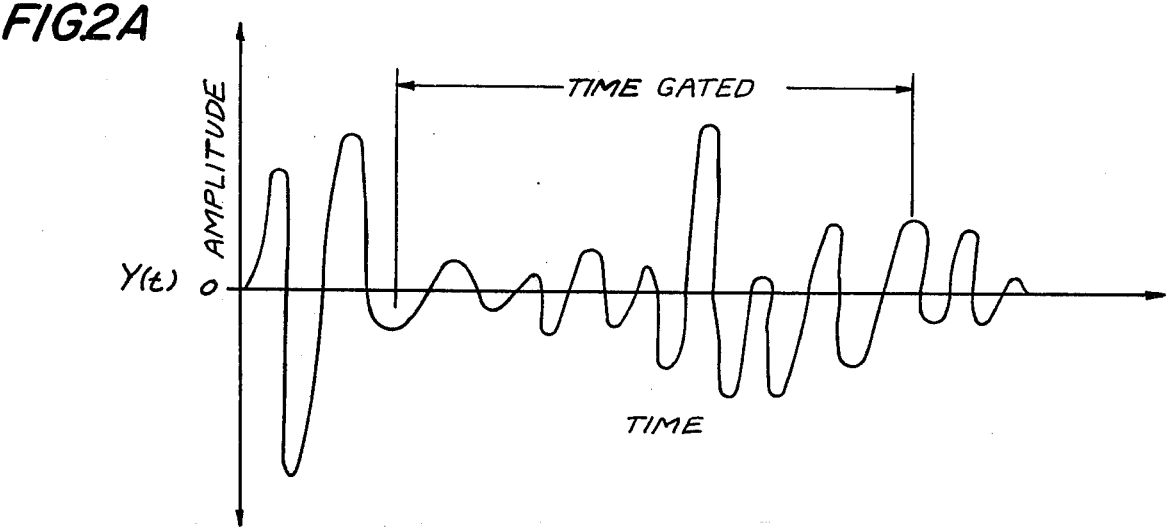
FIGS. 2A, 2B and 2C are graphs drawn to the same amplitude and time scales and respectively illustrate representative plots of an echo signal train in analog and digital form, and a source function in digital form.

Appropriate time gating of the echo signal train, to determined the depth within object 30 at which acoustical interrogation takes place by passing only that portion of the echo signal which emanates from the object depth of interest, is effected by adjustable time gate 44 as indicated in FIG. 2A, and the thusly gated signal is then applied as indicated to pre-filter 46 of appropriate bandpass characteristics. Pre-filter 46 is effective primarily to remove low frequency components of the electrical signal, which low frequency components, in acoustical energy form, were not susceptible of proper focusing by acoustical focusing system 12 and thus contain no useful information. The appropriate filter electrical signal which is, of course, in analog form is then applied as indicated to analog to digital converter 48 for conversion to digital form and application to buffer 50 for signal storage. Although not shown, it may be understood that suitable echo signal compression means in the nature of a log compression amplifier may be interposed between pre-filter 46 and analog to digital converter 48 to insure that the dynamic range of the latter is not exceeded. In like manner, suitable circuit means in the nature of an anti-log circuit would then be interposed between converter 48 and buffer 50 to restore the echo signal to its full dynamic range.

Suitable master clock means are shown at 52 and are operable as indicated at a rate commensurate with the rate of operation of exciter and source function generator 34 to control the rate of operation of adjustable time gate 44, analog to digital converter 48, buffer 50, reference signal buffer and Fast Fourier Transforms as indicated respectively at 56, 54 and 58, and all other digital components of the impulse response computer 15 as described in greater detail hereinbelow. Suitable time delay means (not shown) may, of course, be utilized as and where required to insure proper operational timing of said digital components.

Figure 2B:
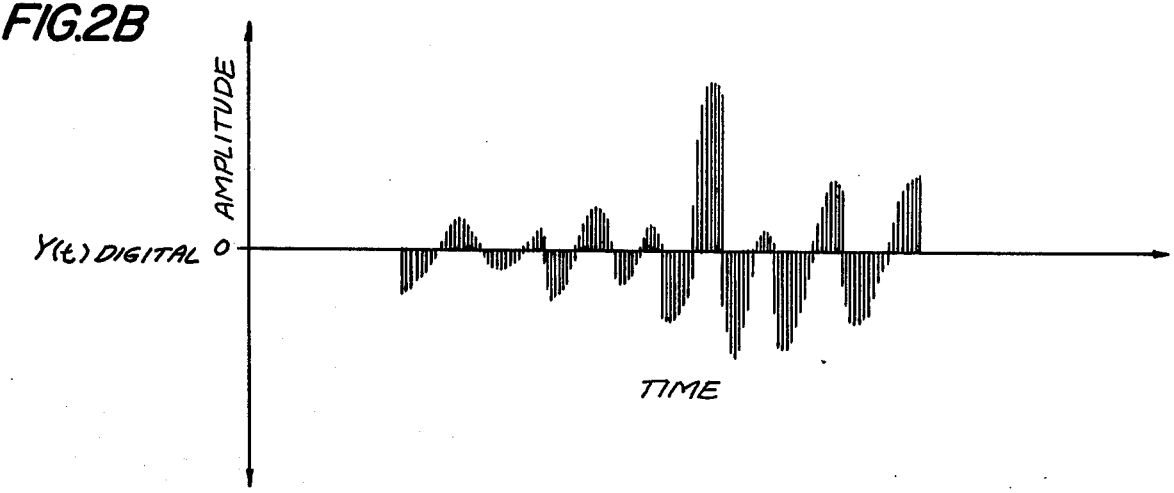

Upon command from clock means 52 the now digitalized or digitally sampled echo signal, which may for example take the form of that indicated at Y(t) Digital in FIG. 2B, is applied as indicated to Fast Fourier Transformer 54 which is of appropriate bin size commensurate with the sampling rate of converter 48 and which functions upon command from clock 52 to transform the Y(t) Digital information of FIG. 2B from the time domain to the frequency domain to significant advantage for deconvolution purposes as compared to deconvolution in the time domain. More specifically deconvolution in the frequency domain may be understood to be reduced to a basic division process, as described in detail hereinbelow, to enable the determination of the epoch or arrival time of each echo signal, to simplify pre and post deconvolution signal processing in the nature of filtering and/or band limiting, and to render more readily apparent, and thus more readily reasonable and solvable, mathematical instabilities in the operation of the deconvolution process.

Concomitantly with the transformation of the Y(t) Digital information from the time domain to the frequency domain by Fast Fourier Transform 54, the source function which represents the best estimate of the ensonifying coherent acoustic source and, as such, includes first reflective surface effects, is applied as indicated under command of clock 52 from buffer 56 to Fast Fourier Transform 58 for transformation from the time to frequency domain. A representative illustration of one such source function in digital form and, of course, plotted as a function of time or in the time domain is indicated at X(t) in FIG. 2C, and it may be understood that this source function may, for example, be obtained by detection of the reflection of a burst of the ensonifying energy from a medium in the nature of a flat plastic plate at the focal plane 28 of focusing system 12, converted from analog to digital converter means which operate at the same sampling rate as converter 48, and permanently loaded into buffer 56 for repeated application therefrom to Fast Fourier Transform 58 at a rate determined by clock 52. Alternatively, this source function may be determined in situ by appropriate detection, processing and conversion to digital form in the manner described in detail hereinabove for echo signal Y(t).

Figure 2C:
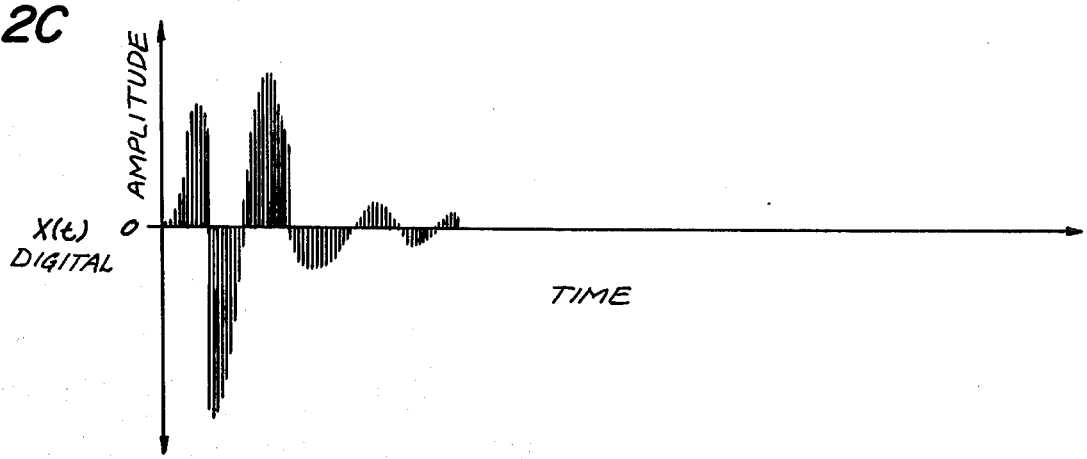

Deconvolution as utilized herein is based upon a comparison to the known acoustic source function X(t) of FIG. 2C, it being noted that minimum distortion of the latter and its component frequency spectra due to spatial effects related to the dimensions of the focusing system 12 is achieved by precise control of said dimensions as discussed hereinabove. The X(t) wave form which exists for a short period of time, only, can be described in the frequency domain as X($\omega$) by transformation using the finite fourier transform to result in a function X($\omega$) having a magnitude $|X(\omega)|$ and a phase angle $\phi(\omega)$, both of which are related to the fourier coefficients.

In like manner, the echo signal waveform Y(t) of FIG. 2B can be transformed to a value of Y($\omega$), it being obvious that the echo signal Y($\omega$), in a linear sense, contains waveforms which are replicates of X($\omega$) or X(t) but which are separated in time from each other. The appearance or epoch time of each of these echo signals is related to the structure and dimensions of object 30 where acoustic discontinuities occur to produce the same. Thus may be understood that each of said echo signals is reduced in overall magnitude relative to X(t) and may be opposite in sign or polarity depending upon the gradient of the acoustic impedance which produces the echo signal.

In addition, it is believed clear that the epoch time of one echo signal relative to a preceeding echo signal may result in echo signal overlapping. Since X(t) is of finite duration, each boundary echo $Y_i(t)$ is also of finite duration to thus make clear that if the boundary following $Y_i$ is dimensionally thin, as is often the case when human tissue is concerned, the $Y_{i+1}(t)$ echo signal will begin before the echo signal produced by the $Y_i(t)$ boundary is completed with the result that the net echo signal returned to the transmit and receive switch 36 will be the linear summation of these echo signals as superimposed in time. It thus becomes essential to the maximization of system accuracy that the deconvolution process be reasonably able to detect the presence of overlapped echo signals as described and recover the respective magnitudes of the two echo signals, the different epoch times or separation in time thereof, and the direction and polarity of each of the same.

The simultaneous operation of Fast Fourier Transforms 54 and 58 under command of master clock 52 results in the provision as indicated of the digitized echo signal Y($\omega$) in the frequency domain at the output of the former, and the provision as indicated of the digitized source function X($\omega$) in the frequency domain at the output of the latter. This enables formulation of the basic deconvolution ratio of Equation 1.

$$H(\omega) = Y(\omega)/X(\omega) \qquad \text{Equation 1.}$$

wherein H($\omega$), the ratio of the input signal to the echo signal, represents the impulse response of the object under interrogation in the frequency domain; it being understood that the inverse fourier transform of H($\omega$) will then provide h(t) which is the time domain impulse response of the object in question.

Equation 1, which indicates a division process over the relevant range of the frequency $\omega$, cannot however be performed in a straight-forward manner since X($\omega$) will most probably equal zero at a number of values for $\omega$ to thus result in a denominator of zero in the deconvolution Equation 1 with attendant unacceptable mathematical instability in the same due to the infinite value of H($\omega$) which will be provided at each of said $\omega$ values. Because of this problem, H($\omega$) is calculated through use of the complex forms of X($\omega$) and Y($\omega$), rather than through use of the respective magnitudes and phases thereof, to thus permit advantage to be taken of certain of the properties of the real and imaginary components of these complex forms.

More specifically, if $X(\omega)$ is defined in accordance with Equation 2 as follows:

$$X(\omega) = X_R(\omega) = j\, X_I(\omega) \qquad \text{Equation 2.}$$

and $Y(\omega)$ is defined in accordance with Equation 3 as follows:

$$Y(\omega) = Y_R(\omega) + j\, Y_I(\omega) \qquad \text{Equation 3.}$$

where $$|X(\omega)|^2 = [X_R^2(\omega) + X_I^2(\omega)] \qquad \text{Equation 4.}$$

$$Q_X(\omega) = \tan^{-1}\left(\frac{X_I(\omega)}{X_R(\omega)}\right) \qquad \text{Equation 5.}$$

Similar equations of course exist for $|Y(\omega)|$ and $\phi_y(\omega)$. $H(\omega)$ can be defined by Equation 6 as follows:

$$H_\omega = \frac{Y(\omega) \cdot X^*(\omega)}{|X(\omega)|^2} \qquad \text{Equation 6.}$$

since $$|X(\omega)|^2 = X(\omega) \cdot X^*(\omega) \qquad \text{Equation 7.}$$

Where $$X^*(\omega) = X_R(\omega) - j\, X_I(\omega) \qquad \text{Equation 8.}$$

this results in the following definition for $H(\omega)$ $$H(\omega) = \frac{(X_R \cdot Y_R + Y_I X_I) + j(X_R Y_I - Y_R X_I)}{X_R^2 + X_I^2} = \qquad \text{Equation 9.}$$

$$H_R(\omega) + j\, H_I(\omega)$$

Because the denominator of Equation 9, which is equal to $|X|^2$, can become equal to zero as discussed hereinabove with attendant instability in the deconvolution process, it becomes necessary to analyze the real and imaginary components $X_R(\omega)$ and $X_I(\omega)$ of $X(\omega)$ to avoid such instability. Since $|X|^2$ can equal zero only when both $X_R(\omega)$ and $X_I(\omega)$ are zero, the problem becomes one of deciding what values can be substituted for zero to avoid division by zero and simultaneously not introduce an erroneous estimate of $H(\omega)$ into the deconvolution process. This is here accomplished as described in detail hereinbelow by identifying the values of $\omega$ at which both $X_R(\omega)$ and $X_I(\omega)$ are zero, and then determining the respective first and second derivatives $$\frac{\delta X_R}{\delta\omega}, \frac{\delta^2 X_R}{\delta\omega^2}, \frac{\delta X_I}{\delta\omega}, \frac{\delta^2 X_I}{\delta\omega^2}$$

at these $\omega$ values by utilizing the values of $X_R(\omega)$ and $X_I(\omega)$ at the adjacent $\omega$ values. In so doing, it will generally be found that one of the components will exhibit a finite second derivative with a near zero slope, while the other component will exhibit a finite slope and an inflection point, i.e., $$\frac{\delta^2 X}{\delta\omega^2} = 0.$$

The substitution of a non-zero value is then made for the component where the slope is zero and the second derivative is finite, i.e., the symmetrical component, while the companion component value is permitted to remain at zero. Typically, the $X_R(\omega)$ component will be the symmetrical one and the $X_I(\omega)$ component will exhibit the inflection point. At each value of $\omega$ for which both $X_R(\omega)$ and $X_I(\omega)$ are determined to equal zero, the value substituted for $X_R(\omega)$ will be the average value of $X_R(\omega+1) + X_R(\omega-1)$.

Figure 3A:
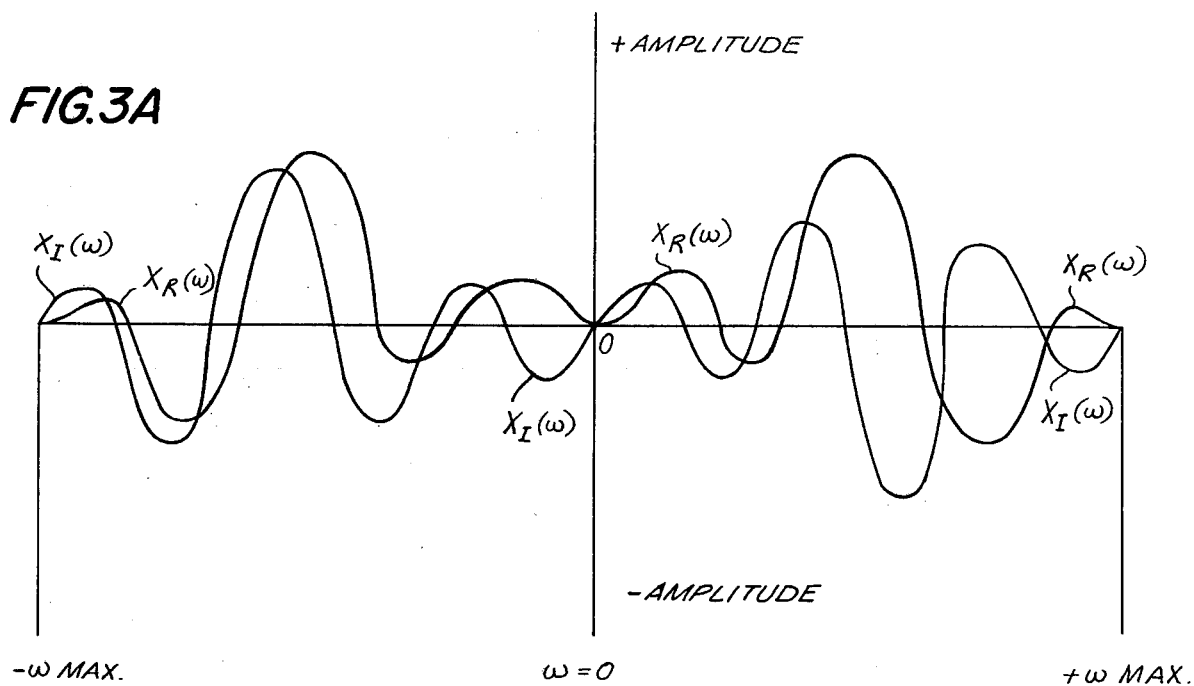
FIGS. 3A and 3B are connected plots of the digital values of the real and imaginary source function components in the frequency domain.

More specifically, and referring now to the connected plots of typical digital values of $X_R(\omega)$ and $X_I(\omega)$ of FIG. 3A, it may readily be seen that these respective real and imaginary components of $X(\omega)$ will, as plotted therein, exhibit coincident zero values at the point where $\omega$ is equal to zero; it being well understood that said components may additionally, or alternatively, exhibit coincident zero values at other and different values of $\omega$.

Figure 3B:
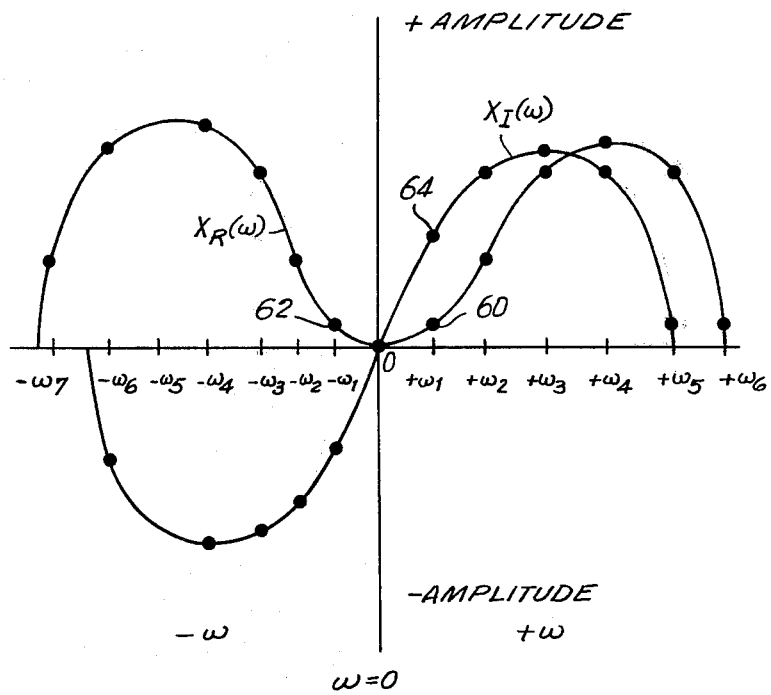

The central portions of the connected plots of the digital value of $X_R(\omega)$ and $X_I(\omega)$ are enlarged in FIG. 3B, and it may be understood that the determination of the value to be substituted for $X_R(\omega)$ or $X_I(\omega)$ at the point where $\omega$ equals zero is determined by calculation of the respective first and second derivatives of the same through use of values of the adjacent digital data points thereof. More specifically, the respective first and second derivatives of $X_R(\omega)$ are calculated through use of the values of digital data points 60 and 62, while the respective first and second derivative of $X_I(\omega)$ are calculated through use of the values of digital data points 64 and 66. In this instance, the first derivative of $X_R(\omega)$ will be zero to indicate a zero slope therefor at the point where $\omega$ is equal to zero and to thus indicate a generally maximum or minimum shape for the $X_R(\omega)$ plot at that point. The second derivative of the $X_R(\omega)$ plot will, however, be finite and the sign thereof will indicate whether the point in question is a maximum point. Conversely, the same calculations with regard to the $X_I(\omega)$ plot will reveal a finite first derivative to indicate a transitional point for that plot where $\omega$ is equal to zero, and a second derivative equal to zero to indicate a constant slope through the coincident zero point of interest. Under these conditions, and in order to arrive at a necessarily non-zero substitutional value for $X(\omega)$ at the point where $\omega$ is equal to zero to avoid an unacceptable mathematical instability in the deconvolution equation while, at the same time, minimizing the distortion of $H(\omega)$ which will be introduced by such substitutional value, the average of the respective values of $X_R(\omega)$ at digital data points 60 and 62 is calculated and substituted for the zero value of $X_R(\omega)$ where $\omega$ is equal to zero, while the zero value of $X_I(\omega)$ at $\omega$ equal to zero is allowed to remain unchanged. Thus, a finite denominator with minimal distortive effects is provided in the basic deconvolution equation.

Referring again to FIG. 1B, it may be seen that the above is accomplished in accordance with the teachings of this invention by application of the respective values for the real and imaginary components $X_R(\omega)$ and $X_I(\omega)$ of the complex $X(\omega)$ numbers from Fast Fourier Transform 58 to comparator 68 for comparison to determined those values of $\omega$ at which coincident values of zero exist for those component values. Concomitantly, these real and imaginary values are applied as shown to buffer 70 for storage.

Comparator 68 is operable to compare the respective $X_R(\omega)$ and $X_I(\omega)$ values, determine at what values of $\omega$ coincident zeros occur therein, and apply these $\omega$ values as indicated to buffer 72. These $\omega$ values, and the respective coincident zero and adjacent values of $X_R(\omega)$ and $X_I(\omega)$ are then applied as indicated from buffers 72 and 70 to logic circuit 74 which is operable to determine the respective first and second derivatives of $X_R(\omega)$ and $X_I(\omega)$ at the relevant values of $\omega$, to determine from said derivatives which of the respective $X_R(\omega)$ and $X_I(\omega)$ values is to be allowed to remain at zero and which is to be replaced by a substitutional value, and to calculate said substitutional value by averaging of the relevant adjacent values as described in detail hereinabove.

The respective values of $X_R(\omega)$ and $X_I(\omega)$ as initially provided from Fast Fourier Transform are then applied as indicated from buffer 70 to buffer 76. Concomitantly, the substitutional value for $X_R(\omega)$ or $X_I(\omega)$, the remaining zero value for the other, and the $\omega$ value at which the same are to be entered in buffer 76, are applied as indicated to the latter from logic circuit 74 to replace the $X_R(\omega)$ or $X_I(\omega)$ zero value by the substitutional value at the appropriate $\omega$ value; and this results in the storage in buffer 76 of a complete set of $X_R(\omega)$ and $X_I(\omega)$ values without coincident zeros at any value of $\omega$.

The respective sets of $Y_R(\omega)$ and $Y_I(\omega)$ values from buffer 78, and the $Y_R(\omega)$ and $X_I(\omega)$ values from buffer 76 are then concomitantly applied to deconvolution filter 80 for operation of the latter in accordance with the basic deconvolution equation as indicated thereon to result in the provision at each of the relevant $\omega$ values of the impulse response $H(\omega)$ in the frequency domain of the object under acoustical interrogation, and the application as indicated of those values to buffer 82. Of particular significance are believe the facts that, through application as described in detail hereinabove of the teachings of this invention to the determination of the $H(\omega)$ values, the mathematical stability of the deconvolution process, and thus of the results provided thereby, is preserved; while the distortion of the value(s) of $H(\omega)$ at the value(s) of $\omega$ wherein both $X_R(\omega)$ and $X_I(\omega)$ were determined to equal zero is minimized through precise determination of the substitutional $X_R(\omega)$ or $X_I(\omega)$ value in accordance with the immediately adjacent and closely related values thereof.

Figure 4A:
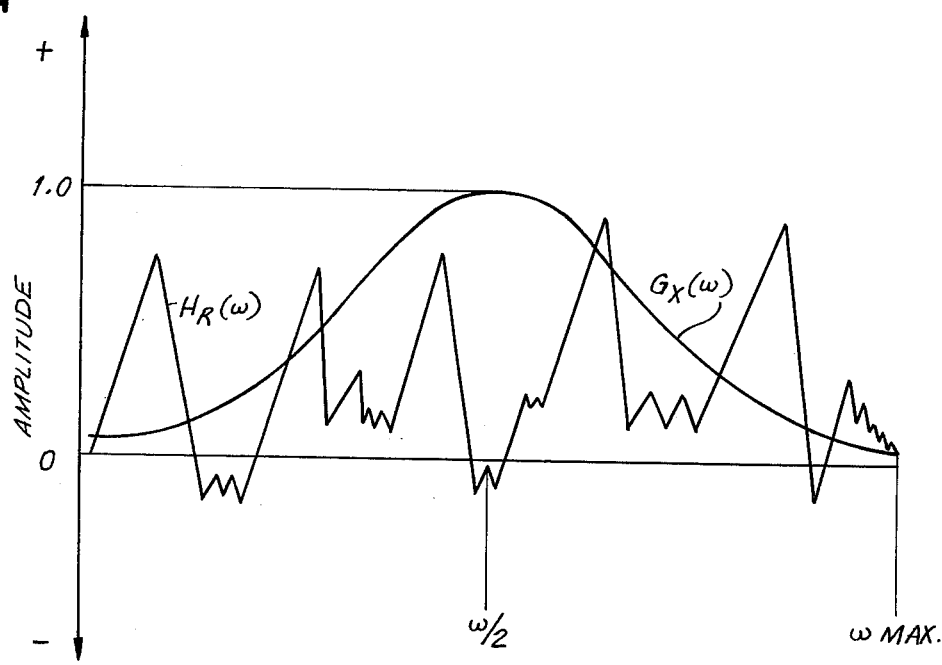
FIGS. 4A and 4B are connected plots of the digital values of the real and imaginary impulse response components in the frequency domain illustrating the multiplication thereof by a noise extraction filter weighting factor.
Figure 4B:
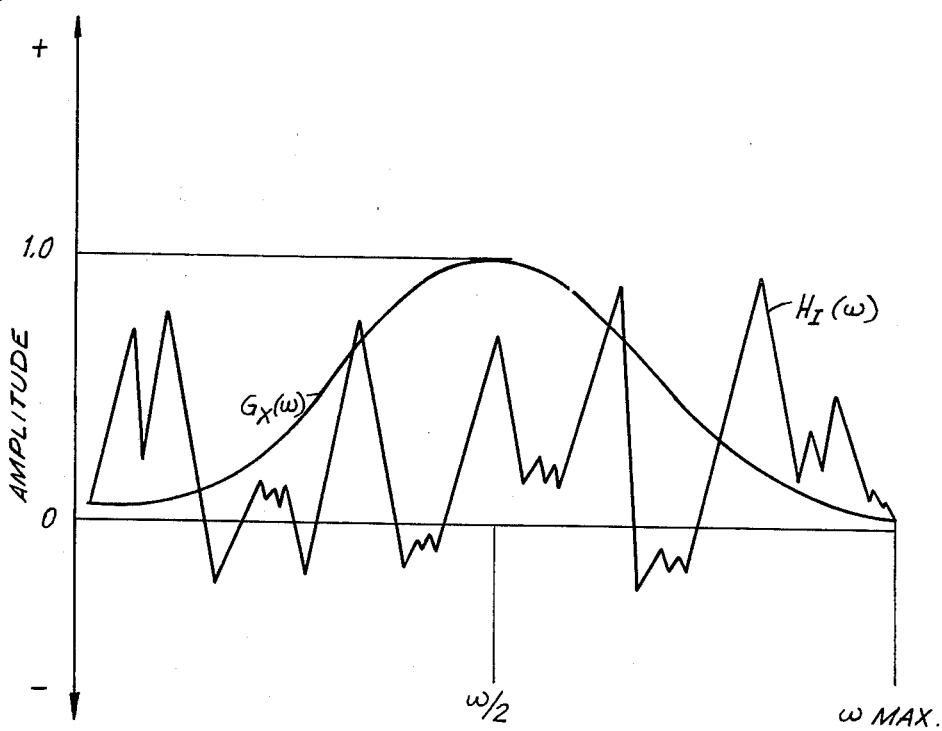

The thusly calculated values for $H(\omega)$, in terms of the respective real and imaginary components $H_R(\omega)$ and $H_I(\omega)$ are applied as indicated from buffer 82 to noise extraction filter 84 which functions to maximize the signal to noise ratio for each of said values. More specifically, connected plots of representative digital values for $H_R(\omega)$ and $H_I(\omega)$ are depicted in FIGS. 4A and 4B and it may be seen that each of the same is multiplied in noise extraction filter 84 by an adjustable and pre-selectable multiplication or weighting factor as indicated at $G_x(\omega)$ which is based on the power spectrum of X and the noise power of the system and is shaped to extract maximum signal to noise from the system. Thus may be seen that the respective $H_R(\omega)$ and $H_I(\omega)$ signals at the skirts of the frequency range which fall below a certain S/N ratio are minimized by the weighting factor $G(\omega)$ relative to those signals which occur near the center frequency and have a better S/N ratio to thereby enhance the overall S/N ratio as provided by the system.

A spatial deconvolution filter is indicated at 85 and is operable in the manner of deconvolution filter 80 to spatially deconvolve the frequency domain impulse response $H(\omega)$ in accordance with a spatial transfer function $S(\omega)$ to minimize the effects on imaging resolution of the distortion of the echo signal train $Y(\omega)$ which can result from non-orthogonally disposed surfaces in the nature, for example, of curved surfaces of the object under acoustical interrogation in accordance with the frequency content of the source function and the geometrical size and configuration of said surfaces in manner dictated by the laws of optics as is believed well understood by those skilled in this art. This problem, and the concept of spatial transforms are discussed in some detail in the work "Systems and Transforms with Applications in Optics" by Dr. Athanasios Papoulis as published in 1968 by McGraw-Hill of New York, and that work is accordingly hereby incorporated by reference herein.

Spatial deconvolution filter 85 is operable as indicated thereon to spatially deconvolve the frequency domain impulse response $H(\omega)$ through complex division thereof by the spatial transfer function $S(\omega)$ as indicated on the filter.

A buffer is indicated at 83, and is utilized to store a multiplicity of arrays of spatial transfer function values, each of which arrays has been predetermined to minimize the distortive effects of non-orthogonally disposed interrogated object surfaces of a different configuration; and it may be understood that each of said arrays of $S(\omega)$ values is selectable at will for application as indicated in spatial deconvolution filter 85 in accordance with the initially observed non-othogonal configuration of the interrogated object surface of interest. For initial signal processing and display, $S(\omega)$ is set at a value of one so that the filter 85 will have no effect on the respective $H(\omega)$ values until a different $S(\omega)$ is selected for application to filter 85 as described in detail hereinbelow.

Application as indicated of the frequency domain impulse response values $H(\omega)$ from filter 85 to inverse Fast Fourier Transform 86 results in the transformation of these values from the frequency to the time domains and the provision of the derived impulse response $h(t)$ in the time domain of the layered material under acoustical interrogation. This derived impulse response is applied as indicated to Raylogram or impedance profile computer 88 which functions in accordance with the equation written thereon in FIG. 1 to compute the Raylographic information of the interrogated material; it being understood that the markedly increased mathematical stability provided as described in detail hereinabove regarding the determination of the transfer function values will, of course, be reflected in the determination as described of the impulse response and Raylographic information values to thus result in the provision of particularly stable Raylographic information. The significance of the provision of this Raylographic or impedance profile information to non-invasive biophysical diagnosis is discussed in some detail in our U.S. Pat. No. 3,830,223 and in our copending application for U.S. Patent, Ser. No. 439,156 filed (now, U.S. Pat. No. 3,934,548) Feb. 4, 1974 and assigned to the assignee hereof, and said application is hereby incorporated herein.

The digital Raylographic information may be applied as indicated directly to digital to analog converter 90 for conversion to analog form, and the resultant analog information applied as indicated to display device 92 (which may for example take the form of an appropriately configured CRT) for real time Raylogram display. Alternatively, the digital Raylographic information may be applied as indicated to buffer 94 for storage and later display as desired.

A spatial driver for the transducer 22 and acoustical focusing system 11 is shown at 96 and is mechanically connected thereto as indicated. For image display, the sequentially provided Raylographic information will be appropriately stored in buffer 94 and the driver 96 will be operable to mechanically drive the acoustical components in precisely predetermined manner relative to the object 30 being acoustically interrogated while transmitting precise positional information to display device 92. Imaging is then accomplished by the timed application of the Raylographic information to the display device 96 in accordance with said positional information to create an image by the retention and build-up of a series of Raylograms on the display device.

Figure 5:
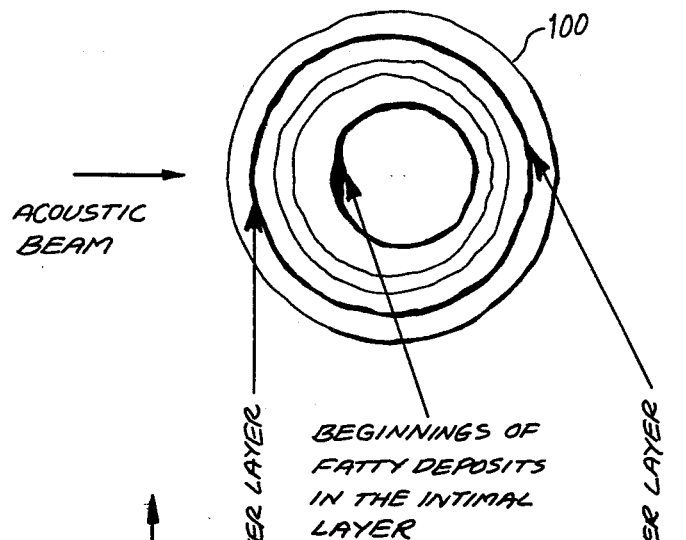
FIG. 5 is a cross-section taken through a human artery.

For use, for example, of the ultrasonic apparatus 10 for the non-invasive acoustical interrogation of a layered material in the nature of a human artery of approximately 5 mm wall thickness as depicted in cross-section at 100 in FIG. 5 for the detection and classification of atherosclerotic plaques and/or other forms of arteriosclerosis, acoustical focusing system 12 may, for example, be arranged to have an acoustical aperture 26 of 400 mm, a system F. stop of 0.87 at the focal plane 28, and to have focal distances 38 and 40 of 200 mm each; while exciter and source function generator 34 and transducer 22 may for example be arranged for the transmission from the latter of broadband acoustical energy pulses having a frequency spectrum or bandwidth ranging from 0.75 mhz to 4.0 mhz.

There are, of course, a large number of factors and/or trade-offs to be considered in determining the bandwidth of the transmitted acoustical energy pulses, and these may be understood to include the thicknesses of the respective layers of the material to be interrogated, the desired acoustical interrogation volume, the generally inverse correlation between axial and azimuthal resolution, the generally direct correlation between increasing frequency and increasing attenuation, the generally direct correlation between increasing frequency and decrease in the smallest size to which the system 12 can be focused down to, the generally direct correlation between decreasing aperture size and decreasing system F. stop, the generally direct correlation between decreasing system F. stop and increasing noise and, the generally direct correlation between decreasing frequency and the required increase in the diameter of the acoustical aperture of the system. In addition, it may be understood that the mathematical deconvolability as described of the echo pulses or echo signal train which result from the acoustical interrogation of the object 30 will play a major role in determining the bandwidth of the acoustical energy, pulses which are transmitted from transducer 22, and in determining the shape and period of the source function which is generated by source function generator 34 and applied to the transducer to result in the transmission of said acoustical energy pulses. Of particular importance in this regard is the choice of focusing system and source function parameters which will minimize the number of points at which the absolute spectral magnitude of source function $X(\omega)$ goes to or closely approaches zero as illustrated in FIG. 3.

In the representative application of the method and apparatus of the invention for detection and classification of atherosclerotic plagues in a pathologic human artery 100 under the source function and focusing system conditions described hereinabove, and assuming in addition the use of Fast Fourier Transforms of 256 element bin size to thus provide for the sampling of the transfer functions $H(\omega)$ at 128 discrete frequencies, an approximate arterial thickness of 5 mm, and a source function or pulse period of 1.5 in seconds, it may be understood that resolution for this example as fine as 40 microns, which is at least one order of magnitude higher than that provided by energy detection despite a shorter pulse period, may be expected from the method and apparatus of the invention.

Figure 6:
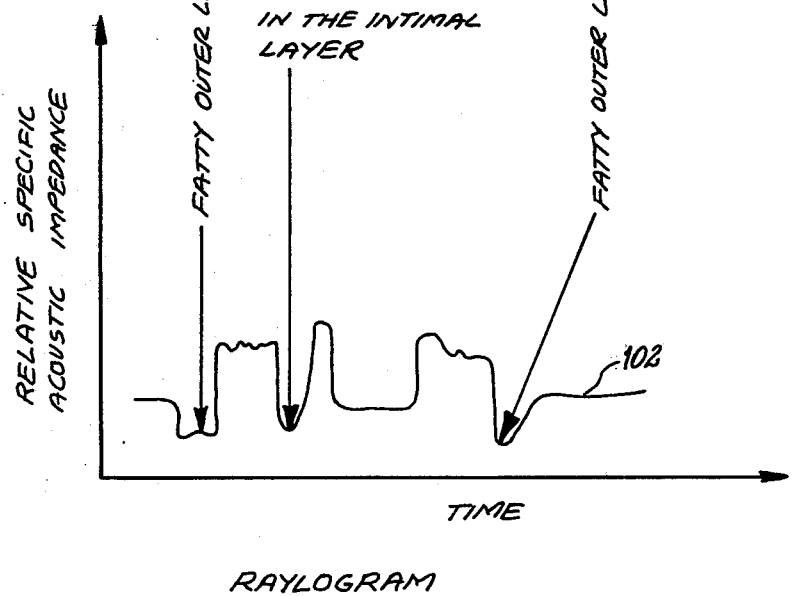
FIG. 6 depicts a Raylogram which may be provided by the ultrasonic apparatus of the invention upon acoustical interrogation of the artery of FIG. 5.

This remarkable resolution with full preservation of phase information and exact indicia of layer boundary dimensions is believed well illustrated by the Raylogram 102 of FIG. 6 which represents the displayed results of the acoustical interrogation of the artery 100 by the method and apparatus of the invention. More specifically, Raylogram 102 renders dramatically detectable the beginnings of fatty deposits in the intimal layer, and clearly distinguishes the same from the fatty outer layer. In addition, clear verification is provided by Raylogram 102 of a non-normal thickened wall condition of the artery 100.

Figure 7:
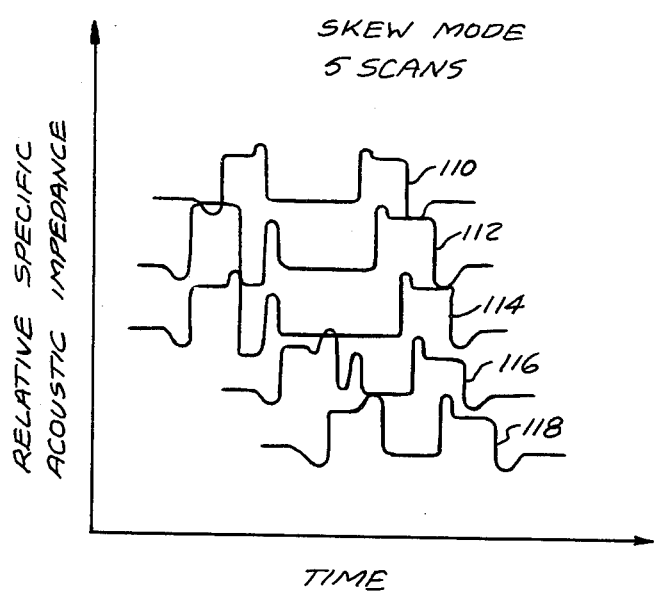
FIG. 7 depicts a skew mode display of a plurality of Raylograms which may be provided by the ultrasonic apparatus of the invention in response to a plurality of lateral scans of the artery of FIG. 5.
Figure 8:
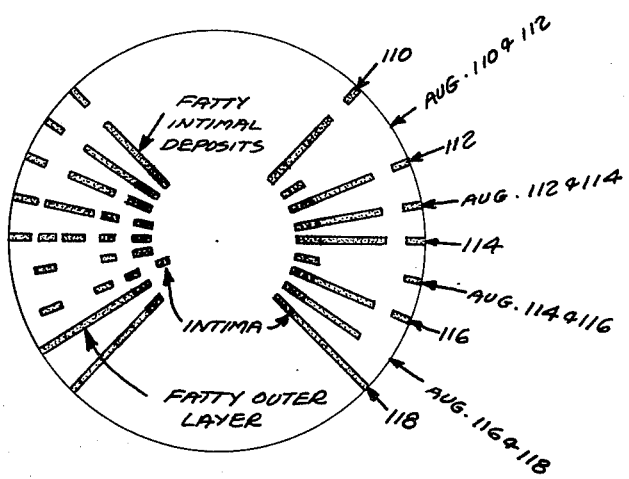
FIG. 8 depicts a B scan display of a plurality of Raylograms which may be provided by the ultrasonic apparatus of the invention in response to a plurality of polar scans of the artery of FIG. 5.

Imaging of the artery 100 can readily be provided by the method and apparatus of the invention as illustrated in FIGS. 7 and 8. More specifically, and referring first to FIG. 7, it may be understood that focusing system 12 is operated under control of spatial driver 96 to achieve five spaced, lateral scans of the artery and, through appropriate use of the storage capability of buffer 94, the resultant Raylograms 110, 112, 114, 116 and 118 can be concomitantly displayed as illustrated as a skew mode display by display means 92 to provide an acoustical impedance image of artery 100 of axial resolution which is markedly superior to that obtainable by use of contemporary energy detection techniques. Operation of spatial driver 96 to achieve five generally radial or polar scans of the artery 100, and the display of the resultant five Raylograms as indicated at 110, 112, 114, 116 and 118, respectively, in the B scan or intensity modulation mode, with interlaced average Raylograms displayed as shown between each basic Raylogram pair to improve spatial recognition, is illustrated by the display of FIG. 8. As a result, the combined improvements in axial and azimuthal, or lateral, resolution provided by the invention will, in the context of the tomogram resulting from the B scan display of FIG. 8, provide for significant improvement in the overall spatial resoution of the display to truly a significant diagnostic advantage.

Further increase in the spatial resolution of the image of FIG. 8 can be provided through appropriate utilization of the spatial deconvolution filter 85 of FIG. 1 C. More specifically, and realizing as discussed hereinabove that said image will initially be provided through application from buffer 83 to spatial deconvolution filter 85 of an array of spatial transfer functions $S(\omega)$ all having a value of one to thus in essence initially negate the function of filter 85, it may be understood that initial observation of the image of FIG. 8 will immediately make clear to the trained observer the nature of the non-orthogonality of the arterial surfaces of interest. This information, coupled with knowledge of the frequency content and basic diffraction pattern of the source function X(t), will enable the educated selection of the array of values for S(ω) from the plurality thereof stored in buffer 83 which is nost appropriate to correct for image distortion caused by arterial surface and boundary non-orthogonality, and application of said array from buffer 83 to spatial deconvolution filter 85. The resultant operation of the filter as described on subsequent data passes there through to complexly divide each of the provided impulse response values H(ω) by the thusly determined value of S(ω) will then function to minimize the distortive effects of non-orthogonality by modification of the H(ω) values as outputted from filter 85 in accordance therewith, with attendant increase in the accuracy of the Raylograms which are generated as described by Raylograms computer 88 in response to said H(ω) values. Accordingly, and since the image of FIG. 8 is composed of a plurality of Raylograms as discussed in detail hereinabove, it may be readily understood that the overall accuracy and resolution of said image will be further improved.

Enlargement of a selected portion of the displayed image may, of course, be readily effected by adjustment of adjustable time gate 44 to reduce that portion of the echo signal train Y(t) which is passed thereby for signal processing and/or appropriate adjustment of the display devise 92 of FIG. 1A to in essence accomplish a "zoom" function in manner well understood by those skilled in this art by restricting the content of the overall image display to a portion, only, of the initially displayed image which is of particular interest. This portion, could, for example, in the case of arterial display, be constituted by that part of the artery which included the beginnings of fatty deposits in the intimal layer as illustrated in FIG. 5, and it may be understood that the above-described procedure would function to fill the face of the display device CRT with that arterial part. Utilization of an appropriate display enlargement technique as described, coupled with operation as described of the spatial deconvolution filter 85 to improve Raylographic accuracy and resolution, should, it is believed, be effective to provide for the imaging of precisely selectable body parts, or portions thereof, with an extremely high degree of spatial resolution.

Additional improvement regarding the interpretability of the tomogram of FIG. 8 can be achieved by the configuration of the display devise to provide a bimodal or two color display. Thus, and assuming by way of example that the two colors chosen for display are green and red, it may be understood that all Raylographic information of intensity above the baseline or reference level—to thus indicate a positive relative specific acoustic impedance—could be displayed as shades of green, while all Raylographic information of intensity at or below the baseline level—to thus indicate a zero or negative relative specific acoustic impedance—could be displayed as shades of red.

Figure 10:
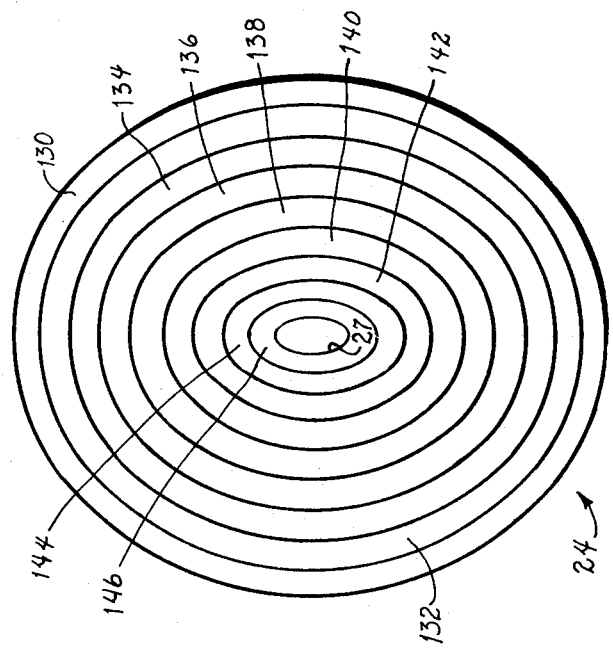
FIGS. 9 and 10 are cross-sectional and end views respectively of a modified acoustic focusing system.
Figure 9:
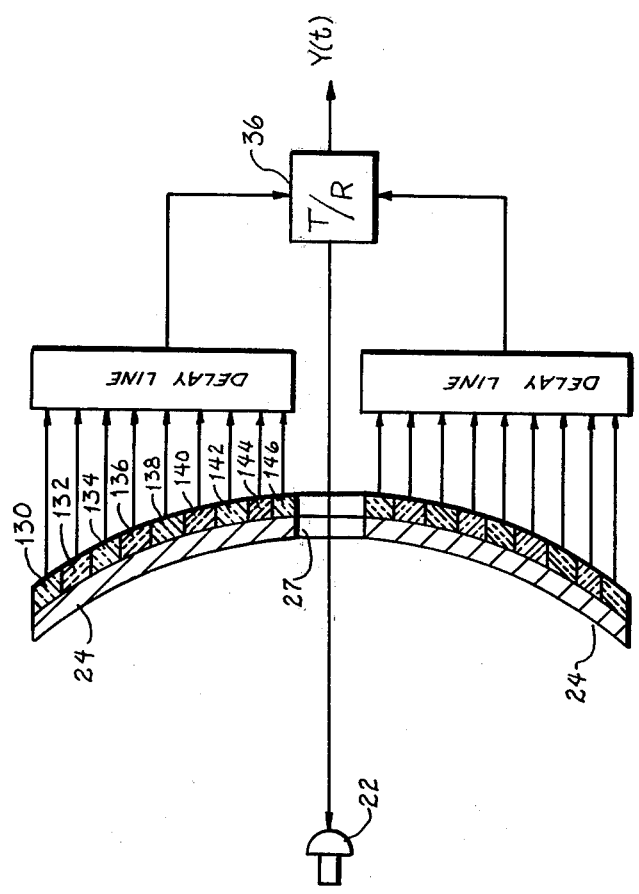

The overall spatial imaging capability of the ultrasonic apparatus 10 can be further enhanced by the modification of the focusing system 12 to provide for independent acoustical signal transmission and reception from and by reflector 24 and enable dynamic system focusing without requiring system movement. More specifically, it may be understood that with a given diameter of reflector 24, appropriate focusing of ultrasound energy can only be achieved at frequencies above a relatively low limit frequency $\omega_L$, the value of which is related to said given reflector diameter. Coherent energy detection assumes coherent energy transmission, and this is of course accomplished by the focusing system 12 as described hereinabove, with the best achievable focused acoustic energy pulse over the permissible frequency range being provided by the smooth operative surface of the elliptical reflector 24. In transmission, the system 12 provides for precise acoustic signal focusing at the system focal point which lies on focal plane 28, and this feature is retained in this modification by retention of the smooth elliptical surface of reflector 24. Echo signal reception is, however, accomplished in this modification as shown in FIGS. 9 and 10 by a plurality of annular rings 130, 132, 134, 136, 138, 140, 142, 144 and 146 of an appropriate piezo ceramic material which are incorporated into the reflector 24 to immediately underlie the smooth reflector surface. Each of said rings is connected as shown through suitable delay line means to the transmit and receive switch 36 for application of the resultant electrical signals to said switch in suitably time-delayed manner. Thus, utilization of appropriate delay line techniques during echo signal reception makes possible precise change in the effective focal point of the focusing system 12 whereby dynamic system focusing is achieved without requiring movement of the reflector 24 and transducer 22. Combination of this delay line technique with spatial driver means 96 having a somewhat limited range of movement can, of course, provide for the direction of the acoustical energy in three dimensions to achieve maximum spatial information. Alternatively, this same capability can be provided for with the acoustical focusing system 12 as depicted in FIG. 1 by utilization of spatial driver means 96 of extensive range of movement.

Various changes may of course be made in the herein disclosed preferred embodiment of the method and apparatus of our invention, and in the variety of parameters and/or limits or operational characteristics or the like herein set forth, without departing from the spirit and scope of our invention as defined in the appended claims.

What is claimed is:

1. In a method for the non-invasive examination of body parts through the selective ensonification of at least a portion of a body part with acoustical energy pulses to produce acoustical energy echo pulses, and the detection and processing of said echo pulses to indicate the relative specific acoustic impedance of the thusly ensonified body part, the steps of, transforming said echo pulses from the time domain to the frequency domain throughout a predetermined frequency range, deconvolving said echo pulses in the frequency domain to determine the impulse responses in the frequency domain of the ensonified body part at a plurality of frequencies within said frequency range, and determining the impulse responses of the ensonified body part in the time domain by transformation of said impulse responses from the frequency domain to the time domain.

2. In a method as in claim 1 wherein, said transformations are complex Fourier transformations.

3. In a method as in claim 1 wherein, the ensonification of said body part comprises the coherent transmission of said acoustical energy pulses, and the detection of said acoustical energy echo pulses is coherent to preserve both the amplitude and phase information which is inherent in said pulses.

4. In a method as in claim 1 further comprising, the steps of successively ensonifying said body part along a plurality of spaced generally parallel planes to provide indicia of the relative specific acoustic impedance thereof along each of said planes, and concomitantly displaying said indicia on a CRT or like display device in skew display mode to provide an image of said body part.

5. In a method as in claim 1 further comprising, the steps of, successively ensonifying said body part along a plurality of acurately displaced generally radial planes to provide indicia of the relative specific acoustic impedance thereof along each of said planes, and concomitantly displaying said indicia on a CRT or like display device in intensity display mode to provide a tomographic image of said body part.

6. In a method as in claim 1 wherein, the deconvolution of said echo pulses comprises, the steps of, detecting said ensonifying energy pulses, and transforming said ensonifying energy pulses from the time domain to the frequency domain.

7. In a method as in claim 6 wherein, said transformations are complex Fourier transformations, and the deconvolution of said echo pulses comprises, stabilizing said impulse responses in the frequency domain by replacing unstable values of the complex representations of said ensonifying energy pulses in the frequency domain with substitutional values which are calculated from said complex representations to minimize distortion of said impulse response thereby.

8. In a method as in claim 6 wherein, said transformations are complex Fourier transformations, and the deconvolution of said echo pulses is accomplished in accordance with the following equation:

$$H(\omega) = \frac{[X_R(\omega) \cdot Y_R(\omega) + Y_I(\omega) \cdot X_I(\omega)] + j[X_R(\omega) \cdot Y_I(\omega) - Y_R(\omega) \cdot X_I(\omega)]}{X_R^2(\omega) + X_I^2(\omega)}$$

wherein:
$Y_I(\omega)$ is the imaginary component of the echo pulses in the frequency domain,
$X_R(\omega)$ is the real component of the ensonifying energy pulses in the frequency domain,
$Y_R(\omega)$ is the real component of the echo pulses in the frequency domain,
$X_I(\omega)$ is the imaginary component of the ensonifying energy pulses in the frequency domain, and
$H(\omega)$ is the impulse response of the body part in the frequency domain.

9. In a method as in claim 8 wherein, in the event of coincident zero values for $X_R(\omega)$ and $X_I(\omega)$ at the same frequency $\omega$, substitutional values for one or the other thereof are calculated through use of the $X_R(\omega)$ or $X_I(\omega)$ values at the adjacent frequencies $\omega$ of interest, and said substitutional values are utilized in lieu of said zero $X_R(\omega)$ or $X_I(\omega)$ value in the equation to prevent the equation denominator from going to zero while minimizing distortion of the provided $H(\omega)$ values.

10. A method as in claim 9 wherein, the determination of which of the coincident zero values of $X_R(\omega)$ and $X_R(\omega)$ is to be substituted for is made by calculating the respective first and second derivatives of $X_R(\omega)$ and $X_I(\omega)$ at the frequency $\omega$ at which the coincident zero values appear by use of the respective values of $X_R(\omega)$ and $X_I(\omega)$ at the adjacent frequencies $\omega$ and substituting for that component which exhibits a zero or near zero first derivative and a finite second derivative.

11. In a method as in claim 9 wherein, the calculation of the substitutional value is effected by averaging the summation of the values of the component to be substituted for at the adjacent frequencies $\omega$ of interest.

12. A method as in claim 10 wherein, the calculation of the substitutional value is effected by averaging the summation of the values of the component to be substituted for at the adjacent frequencies $\omega$ of interest.

13. A method as in claim 1 further comprising, the steps of, spatially deconvolving said impulse responses in the frequency domain to minimize the distortive effects of non-orthogonally disposed portions of said body part on said impulse responses.

14. In a method as in claim 13, wherein, said spatial deconvolution comprises the complex division of said impulse responses in the frequency domain by a spatial transfer function which is calculated in accordance with said non-orthogonality.

15. In a method as in claim 12 further comprising, the steps of, spatially deconvolving said impulse responses in the frequency domain to minimize the distortive effects of non-orthogonally disposed portions of said body part, said spatial deconvolution comprising the complex division of said impulse responses in the frequency domain by a spatial transfer function which is calculated in accordance with said non-orthogonality.

16. In a method as in claim 6 further comprising, the steps of, complexly multiplying the real and imaginary components $H_R(\omega)$ and $H_I(\omega)$ of the impulse response $H(\omega)$ in the frequency domain by the same weighting factor which is variable in accordance with the power spectrum of the ensonifying energy pulses to maximize the signal to noise ratio.

17. In a method as in claim 7 wherein, the ensonification of said body part comprises the coherent transmission of said acoustical energy pulses, and the detection of said acoustical energy pulses is coherent to preserve both the amplitude and phase information in said pulses.

18. In a method as in claim 15 further comprising, the steps of, complexly multiplying the real and imaginary components $H_R(\omega)$ and $H_I(\omega)$ of the impulse response $H(\omega)$ in the frequency domain by the same weighting factor which is variable in accordance with the power spectrum of the ensonifying energy pulses to maximize the signal to noise ratio.

19. In apparatus for the non-invasive examination of body parts through the selective ensonification of at least a portion of a body part with acoustical energy pulses to produce acoustical energy echo pulses, and the detection and processing of said echo pulses to indicate the relative specific acoustic impedance of the thusly ensonified body part, the improvements comprising, means for transforming said echo pulses from the time domain to the frequency domain throughout a predetermined frequency range, means for deconvolving said echo pulses in the frequency domain to determine the impulse responses in the frequency domain of the ensonified body part at a plurality of frequencies within said frequency range, and means for determining the impulse response of the ensonified body part in the time domain by transformation of said impulse responses from the frequency domain to the time domain.

20. In apparatus as in claim 19 wherein, said transformation means comprise Fast Fourier Transforms.

21. In apparatus as in claim 19 wherein, the ensonification of said body part by acoustical energy pulses is effected by coherent pulse transmission means, and the detection of the resultant echo pulses is effected by coherent pulse detection means to preserve both the amplitude and phase information which is inherent in said echo pulses.

22. In apparatus as in claim 19, further comprising, means for successively ensonifying said body part along a plurality of spaced, generally parallel planes to provide indicia of the relative specific acoustic impedance thereof along each of said planes, and CRT or like display means for concomitantly displaying said indicia in skew display mode to provide an image of said body part.

23. In apparatus as in claim 19, further comprising, means for successively ensonifying said body part along a plurality of arcuately displaced, generally radial planes to provide indicia of the relative specific acoustic impedance thereof along each of said planes, and CRT or like display means for concomitantly displaying said indicia in intensity display mode to provide a tomographic image of said body part.

24. In apparatus as in claim 19 wherein, said deconvolution means comprise means for detecting said ensonifying energy pulses, and means for transforming the same from the time to the frequency domain.

25. In apparatus as in claim 19 wherein, said means for deconvolving said echo pulses further comprise, means for stabilizing said impulse responses in the frequency domain by replacing unstable values of the complex representations of said ensonifying energy pulses in the frequency domain with substitutional values which are calculated from said complex representations to minimize distortion of said impulses responses thereby.

26. In apparatus as in claim 19 wherein, said deconvolution means comprise a deconvolution filter which is operable in accordance with the following equation:

$$H(\omega) = \frac{[X_R(\omega) \cdot Y_R(\omega) + Y_I(\omega) \cdot X_I(\omega)] + j[X_R(\omega) \cdot Y_I(\omega) - Y_R(\omega) \cdot X_I(\omega)]}{X_R^2(\omega) + X_I^2(\omega)}$$

Wherein:
$X_R(\omega)$ is the real component of the ensonifying energy pulses in the frequency domain,
$Y_R(\omega)$ is the real component of the echo pulses in the frequency domain,
$X_I(\omega)$ is the imaginary component of the ensonifying energy pulses in the frequency domain,
$Y_I(\omega)$ is the imaginary component of the echo pulses in the frequency domain, and
$H(\omega)$ is the impulse response of the body part in the frequency domain.

27. In apparatus as in claim 26 wherein, said deconvolution means further comprise comparator and logic circuit means which are respectively operatively connected to said deconvolution filter and are operable, in the event of coincident zero values for $X_R(\omega)$ and $X_I(\omega)$ at the same frequency $\omega$, to calculate a substitutional value for one or the other thereof through use of the respective $X_R(\omega)$ and $X_I(\omega)$ values at the adjacent frequencies $\omega$ of interest, and to apply said substitutional value to said deconvolution filter in lieu of said zero $X_R(\omega)$ or $X_I(\omega)$ value in the equation to prevent the equation denominator from going to zero while minimizing distortion of the provided $H(\omega)$ values.

28. In apparatus as in claim 19, further comprising means for spatially deconvolving said impulse responses in the frequency domain to minimize the distortive effects of non-orthogonally disposed portions of said body part on said impulse responses.

29. In apparatus as in claim 28 wherein, said spatial deconvolution means comprise a spatial deconvolution filter which is operable to complexly divide said impulse responses in the frequency domain by a spatial transfer function which is calculated in accordance with said non-orthogonality.

30. In apparatus as in claim 27, further comprising, means for spatially deconvolving said impulse responses in the frequency domain to minimize the distortive effect of non-orthogonally disposed portions of said body part, said spatial deconvolution means comprising a spatial deconvolution filter which is operable to complexly divide said impulse responses in the frequency domain by a spatial domain by a spatial transfer function which is calculated in accordance with said non-orthogonality.

31. In apparatus as in claim 19, further comprising, noise extraction filter means operatively connected to said deconvolution means and operable to complexly multiply the real and imaginary components $H_R(\omega)$ and $H_I(\omega)$ of the impulse response $H(\omega)$ in the frequency domain by the same weighting factor which is variable in accordance with the power spectrum of the ensonifying energy pulses to maximize the signal to noise ratio.

32. In apparatus as in claim 30, further comprising, noise extraction filter means operatively connected to said deconvolution means and operable to complexly multiply the real and imaginary components $H_R(\omega)$ and $H_I(\omega)$ of the impulse response $H(\omega)$ in the frequency domain by the same weighting factor which is variable in accordance with the power spectrum of the ensonifying energy pulses to maximize the signal to noise ratio.

33. In apparatus as in claim 19 wherein, the ensonification of said body part with acoustical energy pulses and the detection of the resultant echo pulses are effected by an acoustical focusing system, said system comprising, a substantially elliptical acoustical reflector having a smooth reflecting surface which forms an acoustical aperture, a convex receiver/projector transducer spaced from said reflector and disposed in substantial alignment with the major axis of the reflector within the field of said acoustical aperture, said transducer comprising a substantially spherical surface facing said reflector and having a radius of curvature R, said acoustical reflector having first and second spaced acoustical focal points, said transducer being located between said second focal point and said reflector and being so disposed relative to said reflector that the center of the radius of curvature R is substantially coincident with said first acoustical focal point.

34. In apparatus as in claim 33 wherein, the distance along the major axis of the reflector between said first and second focal points is substantially equal to the distance along said major axis from said first focal point to said reflector.

35. In apparatus as in claim 33 wherein, said reflector comprises a plurality of piezoelectric means disposed immediately to the side of the reflecting surface remote from said transducer and operable to receive said acoustical energy echo pulses in lieu of said transducer, delay line means operatively connected to each of said piezoelectric means and operable to delay the electrical signals generated thereby in response to said acoustical energy echo pulses, whereby said acoustical system may be dynamically focused to re-locate said second focal point through adjustment of said delay line means.

* * * * *